US00PP10741P

United States Patent [19]

Bost

[11] Patent Number: Plant 10,741

[45] Date of Patent: Dec. 29, 1998

[54] HIBISCUS PLANT NAMED 'BOST HYBRID NO. 5'

[76] Inventor: Georgia A. Bost, 1209 Pine Chase, Houston, Tex. 77055

[21] Appl. No.: 912,993

[22] Filed: Aug. 11, 1997

[51] Int. Cl.[6] ..... A01H 5/00

[52] U.S. Cl. ..... Plt./67.8

[58] Field of Search ..... Plt./67.8

*Primary Examiner*—Howard J. Locker

*Attorney, Agent, or Firm*—Martin L. McGregor

[57] ABSTRACT

An herbaceous perennial Hibiscus plant having numerous large polypetalous flowers with pink color, overlapping petal arrangement, a red eye, buds of darker pink, and medium-sized well-branched, upright plants having 3 to 5-lobed leaves of medium green color and distinctive shape and presentation.

1 Drawing Sheet

HISTORICAL NOTE

As of May 1997, there are a total of 23 plant patents granted for the genus Hibiscus in the United States of America. The earliest patented hibiscus plant (U.S. Plant Pat. No. 835), identified in the records simply as 'Mallow', was selected from a population having within its genetic background *Hibiscus laevis* (formerly *militaris*), *H. coccineus,* and *H. moscheutos.* This early improved plant was characterized by having smooth, deeply cut leaves, as attaining shrub height of medium size, of having medium sized (6–8 inch) flowers with deep red, imbricated flower petals and by being adapted for culture in the temperate zone.

Within the remainder of the existing patents, 10 are *H. "rosa-sinensis"* types developed by Frank Moser; three more are also *H. rosa-sinensis* varieties, developed by Roberta Ludick; and one is a variegated sport of *H. paeoniflorus,* selected by Harold Hillis. All plants in this group of patents are developed from tropical, mostly pan-Pacific species that do not survive unprotected north of USDA Zone 10.

The novel plant invention described herein is developed from the suite of perennial hibiscus species belonging to Hibiscus Section Meunchhusia (O.J. Blanchard, 1976; P.A. Fryxell, 1988) that are native to the continental United States. There are four recognized species in this Section (*H. coccineus, H. dasycalyx, H. laevis,* and *H. moscheutos*) one of which has several recognized subspecies: *H. moscheutos moscheutos, H. m. palustris,* and *H. m. grandiflorus.* The other species of Hibiscus native to the conterminous U.S. and Hawaii are not genetically compatible with these four species.

All species of Hibiscus in Section Meunchhusia are wetland plants and, although tolerant of even severe drought (via semi-dormancy), perform best under adequate moisture conditions. They tolerate—rather than require—saturated soil and/or standing water conditions and compete best *in the wild* on the borders of water bodies where periodic fires reduce competition from woody species. Consequently, they make excellent low-maintenance border plantings around water features and grow well in all climates where adequate rainfall and/or irrigation is available. As a general rule, the farther north the planting, the less water is required, the shorter the plant will be at maturity, and the later and shorter will be the period of bloom.

There are currently only nine patented varieties of this type of hibiscus: 'Mallow' (Hemmings, U.S. Plant Pat. No. 835), 'Lady Baltimore' (Darby, U.S. Plant Pat. No. 4,271), 'Anne Arundel' (Darby, U.S. Plant Pat. No. 5,209), 'Sweet Caroline' (Winters, U.S. Plant Pat. No. 7,608), 'Quatro Rojo' (Bost Hybrid No. 1, U.S. Plant Pat. No. 9,311), 'Pink Wonder' (Morrison, U.S. Plant Pat. No. 9,555), and Bost hybrids No. 2 (U.S. Plant Pat. No. 9,852), No. 3 (U.S. Plant Pat. No. 9,851) and No. 4 (U.S. Plant Pat. No. 9,838). The first four of these plants were developed from East Coast USA populations of Hibiscus species (or subspecies) *H. moscheutos, H. moscheutos* ssp. *palustris,* and/or *H. laevis,* in various combinations with the Florida species, *H. coccineus. The sixth was developed from H. moscheutos, H. m. palustris* and *H. laevis*. 'Quatro Rojo' and Bost hybrids 2, 3 and 4 were developed from progeny of crosses made with a population of *H. laevis* native to Texas, in various combinations with *H. coccineus* and *H. moscheutos*×*'Southern Belle'; the latter was developed from U.S. native hibiscus by U.S. and Japanese breeders many years ago and marketed in the USA, originally through seed catalogs. 'Southern Belle' is dominated by H. moscheutos* characteristics and tends to be true to type from seed for form and color (except for pinks).

The general growh habit of Section Meunchhusia hibisci is characterized by long, straight, light-weight canes which arise annually from a perennial crown. Once established, crowns generally bud two to three—more rarely, four—new shoots from the base of each of the preceeding season's canes. Side branching occurs in the upper half to one-third of the cane (depending on species dominance), given sufficient length of growing season. but generally is not initiated until first bud set has occurred. Earlier branching of canes occurs only if top of the green cane is cut or broken off.

All four native species in Section Meunchhuisa are more likely to self pollenate than to outcross, but each species has a diffrent mechanism for this phenomen. *H. coccineus* is the only wild member of the group that is not bee-pollenated, and shows very little variation between wild populations. The other three species show striking variations across and within their ranges. *H. dasycalyx* is now considered to be a probable subspecies of *H. laevis* (R.A. Klips, Am. Journal of Botany 82(11):1463–1472, 1995).

The crowns of perennial hibiscus frequently go through cycles of cane production that are a function of the age of the crown and the amount of crowding in the center of the crown. Typically, new canes are more abundant on the outside of the crown, until enough space has developed in the center to once again allow central cane growth. Plants can be propagated effectively either from crown division or from cane cuttings when green; for either method, rooting hormone is optional.

Cane production is typically much more vigorous (in both size and number) in hybrids than in the native specimens, all other factors being equal. In general, a new seedling will produce only one cane, due to the time it takes for the plant to mature enough to begin flower budding. Second year crowns generally break dormancy with 2–3 canes, but may produce more given a sufficiently long growing season. Third year crowns typically produce 6–9 canes, and so on. Number and vigor of canes is also dependent on spacing of the individual specimens and the size of the container in which it is grown, as well as length of growing season where grown and the genetic background of the parental stock from which the cultivar was developed. Plants become severely stunted when container size is too small for the crown size. A well developed crown will frequently outweigh its canes.

Spacing of leaves, internodal length and leaf shapes are a function of species genome, as is bloom onset and distribution, abscission point, and presence or absence of foliage on bloom pedicels. However, these characters *in hybrids* show a wide range of intermediate characters and may or may not be distinctive for a given hybrid type.

Overall plant presentation ranges from *H. moscheutos* on one extreme, with an essentially spherical shape (consisting of relatively short canes and widely-spaced but large, cordate leaves), to *H. coccineus* on the other extreme, with all essentially vase-shaped or V-shaped presentation of 5-lobed, highly-dissected, Cannibis-like leaves. *H. laevis* and *H. dasycalyx* have the shortest internode size with leaves that are predominantly 3-lobed and hastate, with an essentially vase-shaped habit. *H. moscheutos* (including *H.m. palustris* and *H.m. grandiflorus*) flower buds tend to produce a panicle-like effect due to the extreme fore-shortening of flowering internodes and the relatively short period of flowering for this species (1–2 months, even in Zone 9). The other three species have well-spaced flowers that follow the same rotation as the leaf nodes and bloom for 2–7 months, depending on soil temperatures and frost dates for the region in which they are grown, and genetic dormancy for the region of origin.

On the average, a given flower for any of these genomes will last only one day; however, cool nights followed by cool mild day(s) commonly delay flower drop for an additional day or two, especially if pollenization has not occurred. The farther north the plants are grown, the more likely the flowers are to last more than one day. Thus, the ability of a given flower to last more than one day is not a particularly distinctive character within this group. Similarly, the more northern USDA Zones will have shorter and more concise bloom periods and may frequently experience frost before "natural" dormancy begins. The regional affect on the genetic component of dormancy appears to apply primarily to the breaking of dormancy in the spring, not to winter onset.

In Zone 9, dormancy almost always occurs before frost, although some plants have still been observed to bloom as late as the end of January during especially mild winters. Dormancy appears to be triggered by soil temperature, but also shows a strong genetic component related to the climatic region of the source genome. Dormancy or semi-dormancy can also be triggered by severe drought. A normal winter-triggered dormant period seems to be beneficial for this group of Hibiscus, as specimens grown in tropical climates or in heated greenhouses year-round lose vigor, are less resistant to disease and pests, and eventually die prematurely (five years or less).

The average life span of the perennial crowns of these species and their hybrids has not, to our knowledge, been documented. Anecdotal evidence suggests crown life-spans of more than 25 years and, barring catastrophic events or disease, could be more than 100 years. The average is probably 10-20 years.

BACKGROUND OF THE NEW PLANT

The breeding program which produced the novel plant invention described herein and named 'Bost Hybrid No.5' extended over a period of more than 11 years. 'Bost Hybrid No . 5' is one of many seedlings selected from progeny of cross pollination between (1) a breeding line derived from crossing the commercially available *H. moscheutos* var. 'Southern Belle' and *H. laevis* BOSTx® selection 'Houston-White'; (2) a breeding line derived from crossing *H. laevis* BOSTx® selection 'Houston-White' and *H. coccineus;* and/or, (3) a breeding line derived from crossing *H. coccineus* and *H. moscheutos* var. 'Southern Belle'. 'Bost Hybrid No. 5' is a product of crossing 'Anna Belle Lee' (pod parent) with *H. coccineus 'Lowry' pollen parent).* objective of the breeding program which produced the novel plant of this invention was primarily to develop a plant that was suitable for inclusion in a horticultural group characterized by attractive, well-formed, (large) bicolor flowers that are distinctive for the color and form, that are well-posed on the plant and that remain open for most of the day (two days in cooler weather), and distinctive well-placed foliage of three to (mostly) five-point leaves.

SUMMARY OF THE INVENTION

The present invention comprises a new and distinct cultivar of herbaceous perennial Hibiscus hybrid hereinafter referred to by the cultivar name 'Bost Hybrid No. 5'. It was a seedling selected by Georgia A. Bost in early summer 1992 from a seedling population grown at her nursery, The Village Botanica, Inc., at 7500 Westview Drive, Houston, Tx. She is the owner of the mother plant and clones and controls all propagations of it. The new plant produced its first flower in the summer of 1992 and, because of the size and shape of the plant and the coloring of the flower, its attractive foliage and controlled habit, it was selected for reproduction and testing. Asexual propagation of this new plant by cuttings was carried on at The Village Botanica, 7500 Westview Drive, Houston, Tx. in 1993 and 1994 under the direction of the inventor. Observation of the asexual progeny of the original plant has demonstrated that this new and distinct variety has fulfilled the objectives and that its distinctive characteristics are firmly fixed and hold true from generation to generation.

The new and distinct cultivar is of value for its floral display, produced from late May until late November (or frost), depending upon USDA zone in which it is cultured, environmental conditions and culture methods; and for the landscape value of the entire plant; and as a source of plant materials for commercial and agricultural products.

DETAILED DESCRIPTION OF THE DRAWING

The new cultivar of perennial Hibiscus is illustrated by the accompanying drawing which shows a fully opened flower and some typical leaves and buds, the colors being as true as can reasonably be reproduced by conventional photographic procedures.

DETAILED DESCRPITON OF THE NEW PLANT

The following is a detailed description of the new variety, numerical color terminology being in accordance with The Royal Horticultural Society Colour Chart (indicated by initials R.H.S.-number) for the closest match, or with ordinary dictionary significance.

The plant:

*Type*.—Root-hardy, herbaceous perennial.

*Classification*.—Hybrid variety of Hibiscus, Section Meunchusia(Fryxell, 1988).

*Orgin*.—Seedling.

*Parentage*.—Is known to be a selection from BOSTx® breeding population from cross pollination between (1) a breeding line derived from crossing BOSTx selection 'Anna Belle Lee' (pod parent) with *H. coccineus*.

*Propagation*.—Holds its distinguishing characteristics through succeeding propagations by cuttings and divisions.

*Form*.—Bushy annual growth from perennial roots.

*Mature habit*.—Very upright and somewhat branched, with large, well-presented leaves and flowers.

*Growth*.—Moderate.

*Foliage*.—Arrangement — Alternate. Form — 3 to 5 lobed, incised, palmate. Size — average is 6–8 inches along primary vein, approx.the same width across lateral veins. Central lobe always larger than laterals. Leaf ranges in size to as small as 4 by 2.5 inches and as large as 9 by 9 inches. Margins—dentate. Color — top: Medium green (R.H.S.-146A, R.H.S.-174A in sun). Color — bottom: Light green (R.H.S.-145A to R.H.S.147B/C). Veins — top: Light green (R.H.S.-166B), except in full sun. Veins — bottom: Light green (R.H.S.-145C). Petiole: Length 1¾ to 6 inches. Color — light green (R.H.S.-145A), blushes to (R.H.S.-174A) in full sun. Form: 5-parted to 1-parted, palmately lobed and veined. Stipules: deciduous.

*Stem*.—Cane-like, pale green when young; blushing to light red in full sun and in the fall. Basal cane diameter is approximately 1–2 inches for mature plants.

*Height*.—4.5 to 6.5 feet.

The flower:

*Blooming habit*.—Continuous and free blooming, late May-November (or until frost).

*Corolla*.—Diameter — 7 to 8 inches. The bloom is flat, so the diameter is about the same as the sum of the length of two petals. Shape — Slightly flared, fully open bell with very full petals overlapping distally with distinct open space at eye.

*Involucral bracts.—Number* — 11 (sometimes 10–12). Color—medium green (R.H.S.-144A).

*Calyces*.—Number of sepals — five. Shape — moderately dissected at about ¾ inches from sepal apex, chevron-shaped with apical point at ahout 1.5 inches from base. Color — Pale green (R.H.S.-144B).

*Filaments*.—Color — dark pink (R.H.S.-63B/C).

*Stamens*.—Numerous.

*Stigma*.—Color — whitish pink to pale yellow cream. Size — pads and pedunicles 0.5 inches. Pedicels and peduncle white, pads pale to yellow. Number — five, rounded, discoid, hairy.

*Staminal column*.—Color — white with pink streaks (R.H.S.-63A). Length — 3 inches. Upper ⅔ antheriferous. Base of pistil or very center of throat: red (R.H.S.-53A/B), striped. with dark pink ahout half of the way up.

*Pollen*.—Light yellow (R.H.S.-2B).

*Petalage*.—Shape—Orbicular, apical point right or left of center, depending upon "handedness" of the bloom. Size — 3.5 to 4 inches (base of style to tip of petal), depending upon preceding night temperature and culture. Aspect — central one-third satiny, outer two-thirds opaque Texture — moderately stiff. Color — center eye zone: red (R.H.S.-53A/B). inner petal: very light pink-white (R.H.S.-58B/62B). Middle petal: deep pink (R.H.S.-65C). Outer petal: medium pink (R.H.S.-64C/D). Back of petal: main petal (R.H.S.-65A/62-63D). White eye zone (R.H.S.-155A-55B/C). The overall effect is of a large tricolor flower with a dinner plate shape. Much of the color pattern is due to diferent matrix colors; vein color is deep pink throughout, deepening to red near the eye.

*Flower*.—Numerous, elegant; individual flowers last one day, two days in cooler weather.

*Peduncle*.—1.5 to 2.5 inches; medium thickness; very stiff. Articulated at or near about 2.5 inches from the top.

General characteristics and culture:

*Blooming Period*.—Late May to November (or frost) on the Texas Gulf Coast (Zone 9), July or early August to frost in cooler zones. From the onset of the blooming period the plant is seldom without flowers.

*Hardiness*.—Root hardy to at least Zone 5 (further North if well mulched). Dormancy is apparently triggered by soil temperatures rather than by photoperiod. Research at Michigan Sttate indicates that Hibiscus plants in this group are day-neutral bloomers.

*Breaking action*.—Very tough. Immature stems bend and regrow.

*Rooting*.—Excellent. Hormone optional, epecially under mist.

*Growth regulator*.—Not required. Optional for holding in pots for commercial nurseries.

*Shipping tolerance*.—Excellent, especially as liners or at any size when dormant. Best shipped unstacked in rows on individual shelves, if not-dormant.

I claim:

1. A new and distinct cultivar of Hibiscus plant, substantially as shown and described.

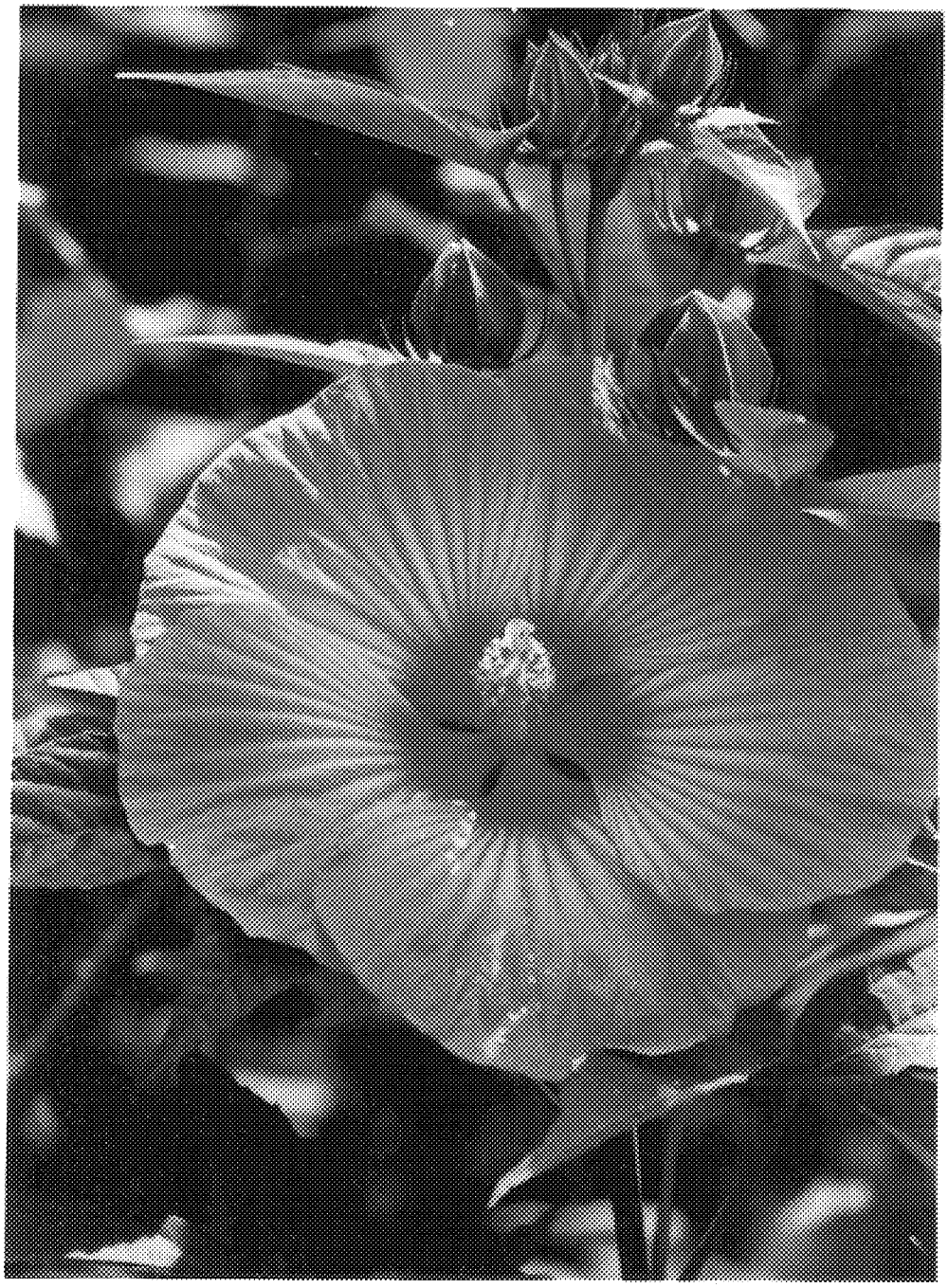

* * * * *